United States Patent [19]

Lecolier et al.

[11] 4,077,964
[45] Mar. 7, 1978

[54] CARBAMATE-PHOSPHONATES, AND PROCESS OF PREPARATION

[75] Inventors: Serge L. Lecolier, Janville-sur-Juine; Jean-Marie J. Biehler, Brunstatt, both of France

[73] Assignee: Societe Nationale des Poudres et Explosifs, France

[21] Appl. No.: 614,706

[22] Filed: Sep. 18, 1975

[30] Foreign Application Priority Data

Oct. 17, 1974 France .................. 74.34948

[51] Int. Cl.² .............. C07D 207/08; C07D 211/32; C07F 9/40
[52] U.S. Cl. .................. 260/293.86; 260/326.4; 260/938; 260/2.5 AJ
[58] Field of Search ............. 260/293.86, 293.88, 260/326.4, 938

[56] References Cited

U.S. PATENT DOCUMENTS

| 3,690,941 | 9/1972 | Reuter et al. | 117/136 |
|---|---|---|---|
| 3,758,554 | 9/1973 | Gaj | 260/482 B |
| 3,763,283 | 10/1973 | Curgan | 260/938 |
| 3,835,204 | 9/1974 | Weil | 260/938 |
| 3,899,548 | 8/1975 | Petersen et al. | 260/932 |
| 4,029,679 | 6/1977 | Kotzsch et al. | 260/938 |

FOREIGN PATENT DOCUMENTS 2,046,777  3/1971  France.

*Primary Examiner*—John M. Ford
*Attorney, Agent, or Firm*—Bucknam and Archer

[57] ABSTRACT

Carbamates of diethyl methylphosphonate of the formula:

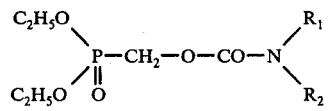

wherein $R_1$ and $R_2$, which may be the same or different, are linear or branched alkyl or hydroxyalkyl radicals containing 2 or 3 carbon atoms, or $R_1$ and $R_2$ together with the nitrogen atom to which they are attached form a ring containing 4 or 5 carbon atoms, or $R_1$ is phenyl and $R_2$ is hydrogen, may be prepared by reacting diethyl hydroxymethyl-phosphonate chloroformate with an amine, and find application in flameproofing rigid or flexible polyurethane foams.

10 Claims, No Drawings

CARBAMATE-PHOSPHONATES, AND PROCESS OF PREPARATION

The present invention relates to certain novel carbamate-phosphonates, to a process for their preparation, and to their use as flameproofing agents, particularly for polyurethane foams.

Non-reactive flameproofing agents for polyurethane foams, such as, for example, organic phosphates which may or may not contain halogens, are known. The best-known representative of these non-reactive agents is 2,3-dibromopropyl phosphate. However, polyurethane foams formulated with such flameproofing additives have poor aging resistance and mediocre mechanical properties, because of the tendency of the additive to exude and migrate over a period of time. Furthermore, the fumes evolved during combustion of the foams containing halogenated flameproofing agents are highly corrosive.

Phosphorus-containing flameproofing additives which contain OH groups which participate in the polycondensation reaction between a polyisocyanate and a polyol which takes place in the formation of polyurethane foams, are also known. Such additives are referred to as reactive fameproofing additives. This category of flameproofing additives includes a family of hydroxyalkylaminoalkylphosphonates of which the best-known representative has the formula:

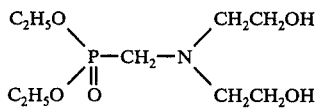

These reactive additives, unlike the above-mentioned non-reactive additives, do not tend to exude from the foam and thus lead to poor aging resistance of the foam. However, the use of these reactive additives is restricted to rigid polyurethane foams and the combustion of foams formulated with such additives releases large quantities of noxious fumes.

It is also known to use compositions based on phosphonate-amides as flameproofing or self-extinguishing agents. Such products are described in, for example, French Pat. Nos. 1,578,091, 2,019,011 and 2,061,303. However, these products also suffer from some of the disadvantages already mentioned, which restricts their field of application.

We have now found that certain novel carbamate-phosphonates are suitable for flameproofing both rigid and flexible polyurethane foams.

According to the invention, there are provided, as novel compounds, carbamate-phosphonates of the formula:

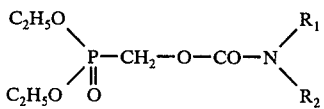

wherein $R_1$ and $R_2$, which may be the same or different, are linear or branched alkyl or hydroxyalkyl radicals containing 2 or 3 carbon atoms, or $R_1$ and $R_2$ together with the nitrogen atom to which they are attached form a ring containing 4 or 5 carbon atoms, or $R_1$ is phenyl and $R_2$ is hydrogen.

The most preferred compound according to the invention is the N,N-bis-(2-hydroxyethyl)-carbamate of diethyl methylphosphonate which is a colourless or yellowish oil, the compound having the formula:

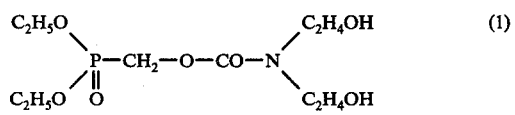

Other preferred compounds of the invention are the N,N-diethylcarbamate of diethyl methylphosphonate:

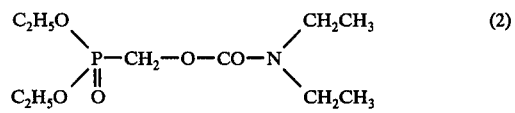

the N-cyclopentamethylenecarbamate of diethyl methylphosphonate:

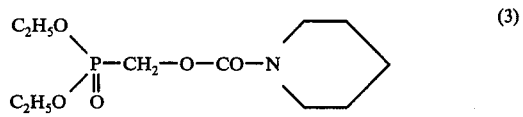

the N-cyclotetramethylenecarbamate of diethyl methylphosphonate:

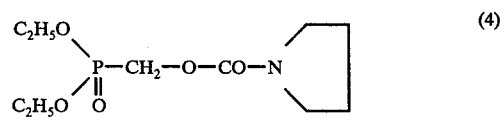

and the phenylcarbamate of diethyl methylphosphonate:

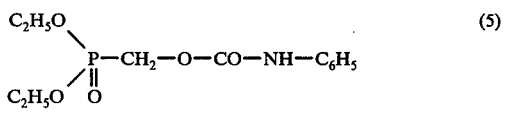

The invention also comprises a method of preparing the carbamate-phosphonates of the invention, which comprises reacting diethyl hydroxymethylphosphonate chloroformate with an amine selected from secondary alkylamines the alkyl groups of which each contain 2 or 3 carbon atoms, dialkanolamines the hydroxyalkyl groups of which each contain 2 or 3 carbon atoms, aniline, pyrrolidine and piperidine, the reaction being effected in the presence of an organic solvent at a temperature below 10° C.

A preferred method of preparing compounds of the invention is the so-called "interfacial condensation" process. In this method, the amine, such as diethanolamine, in a slight excess of 5 to 30% relative to the equimolecular proportion, is dissolved in an aqueous phase containing an alkali metal base such as potassium carbonate, whilst the chloroformate is present in solution in an organic phase. The organic solvent employed must be immiscible with water, sufficiently volatile, inert towards the chloroformate and a good solvent for the final product. Preferred solvents are chlorinated aliphatic hydrocarbons, such as chloroform or dichloromethane.

It is sometimes advantageous to prepare a pre-emulsion by introducing a certain amount of the organic solvent into the aqueous phase and stirring the mixture vigorously before introducing the dissolved chloroformate.

As noted above, we have found that the compounds of the invention are effective flameproofing agents for polyurethane foams. Compounds such as compound (1) which contain hydroxyalkyl groups are reactive flameproofing agents and are thus particularly suitable for flameproofing rigid polyurethane foams. Compounds such as compounds (2) to (5) are non-reactive flameproofing agents.

We have found that best results are obtained when the amount of flameproofing agent incorporated in a polyurethane foam is such that the phosphorus content of the foam is from 0.5 to 2% by weight of the foam.

In order that the invention may be more fully understood, the following Examples are given by way of illustration only:

EXAMPLE 1:

Preparation of the N,N-bis-(2-hydroxyethyl)-carbamate of diethyl methylphosphonate Diethyl hydroxymethylphosphonate chloroformate 40 g of liquid phosgene were introduced into a reactor equipped with a condenser, a stirrer, a dropping funnel and a thermometer. 42 g (0.25 mol) of diethyl hydroxymethylphosphonate prepared by a known method, for example by the reaction of formaldehyde with diethyl phosphonate, were run in slowly. The temperature of the reaction mixture was kept at between $-15°$ C and $-10°$ C whilst the material was being run in. The mixture was then stirred for 4 hours at $-10°$ C and was then allowed to return to ambient temperature, whist stirring. The chloroformate was freed from the excess phosgene and from the dissolved hydrochloric acid by bubbling nitrogen through the mixture, whilst stirring, and was then isolated by filtration.

50 g of the chloroformate was thus obtained as a colourless product, representing a yield of 87%.

N,N-bis-(2-hydroxyethyl)-carbamate of diethyl methylphosphonate

The diethyl hydroxymethylphosphonate chloroformate thus obtained was condensed with diethanolamine in the presence of an alkali metal carbonate as an acid acceptor, in accordance with the following scheme:

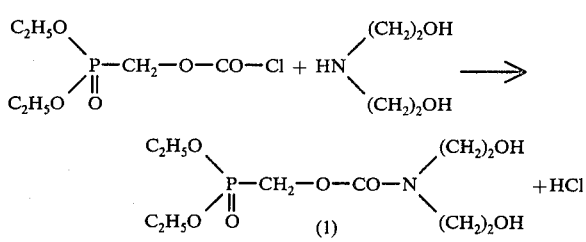

The following were introduced into a reactor equipped with a stirrer and a thermometer: 250 ml of distilled water, 27.6 g (0.2 mol) of potassium carbonate, 26 g (0.25 mol) of diethanolamine and 100 ml of chloroform.

The mixture was cooled to between 0° C and +5° C and 46.1 g (0.2 mol) of diethyl hydroxymethylphosphonate chloroformate dissolved in 400 ml of anhydrous chloroform were allowed to run in slowly over the course of about three hours, whilst stirring vigorously.

The organic phase was collected and the aqueous phase was washed with 100 ml of chloroform. The organic phases were combined, washed with 50 ml of a 2 N hydrochloric acid solution and then with 150 ml of water and finally dried over anhydrous sodium sulphate.

After removing the solvent by evaporation at 60° C under reduced pressure, 32 g of colourless oil were obtained, which was identified as the N,N-bis-(2-hydroxyethyl)-carbamate of diethyl methylphosphonate on the basis of the chemical analysis, and infra-red and NMR spectra data reported below.

Infra-red; an absorption band at 1,710 cm$^{-1}$, characteristic of C=O groups, an absorption band at 1,250 cm$^{-1}$ characteristic of the P=O bond and an absorption band at 975 cm$^{-1}$ characteristic of the P — O — C group.

Nuclear magnetic resonance: The following peaks were observed:

a triplet centered at 1.3 ppm for the CH$_3$ radicals, an unresolved peak at 3.3 to 3.8 ppm for the CH$_2$ groups of the hydroxyethyl radicals, a doublet of quadruplets centered at 4.12 ppm for the CH$_2$ groups separated from the phosphorus atom by an oxygen atom.

and a doublet centered at 4.38 ppm for the CH$_2$ groups attached to the phosphorus atom.

| | Elemental analysis: | | | | |
|---|---|---|---|---|---|
| | C% | H% | N% | P% | OH% content by weight per kg* |
| calculated: | 40.13 | 7.36 | 4.68 | 10.37 | 6.69 |
| found: | 39.9 | 7.48 | 4.59 | 10.4 | 6.58 |

EXAMPLE 2

Preparation of the N,N-diethylcarbamate of diethyl methylphosphonate

Diethyl hydroxymethylphosphonate chloroformate was reacted with diethylamine in accordance with the following scheme:

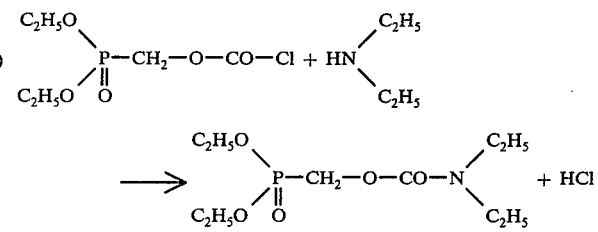

in the presence of an acid acceptor, namely triethylamine.

The following compounds were introduced into a reactor equipped with a cooling system and stirrer: 200 ml of anhydrous ether, 0.3 mol of diethylamine and 0.31 mol of triethylamine.

The temperature of the mixture was kept below 10° C and 0.3 mol of diethyl hydroxymethylphosphonate chloroformate dissolved in 50 ml of anhydrous ether were run in dropwise. The mixture was then stirred for half an hour at 10° C followed by 2 hours at ambient temperature. The triethylamine hydrochloride formed was filtered off and washed with ether. The ether washings were added to the reaction mixture and the ether was evaporated under reduced pressure. The residue was treated with a 10% strength sodium carbonate solution and then extracted with chloroform. The chloroform was removed by heating under reduced pressure at 60° C for 2 hours, to leave, as product, the N,N-diethylcarbamate of diethyl methylphosphonate.

Other compounds according to the invention can also be prepared following the procedure described in Example 1 or 2, by using the appropriate amine to react with the chloroformate. Thus, for example, pyrrolidine, piperidine and aniline respectively yield the compounds denoted above as (4), (3) and (5).

An example of a formulation of a rigid polyurethane foam rendered flameproof by means of the N,N-bis-(2-hydroxyethyl)-carbamate of diethyl methylphosphonate is given below.

| | | |
|---|---|---|
| Polyol TP 440 (trimethylolpropane epoxidised with propylene oxide) | 100 | g |
| Methylene-diphenyldiisocyanate | 132 | g |
| Freon (trichlorofluoroethane) | 30 | g |
| Dibutyl-tin-dilaurate | 0.10 | g |
| N-Methylmorpholine | 1 | g |
| Rhodorsil SI 91-93 (silicone) | 1 | g |
| N,N-Bis-(2-hydroxyethyl)-carbamate of diethyl methylphosphonate (1) | 22 | g (representing 1% by weight of phosphorus). |

A polyurethane foam formed from the above formulation had a density of 50 g/liter and its critical pressure was 2.8 bars.

This foam, which will be referred to as foam A, was subjected to comparative experiments with, firstly, a polyurethane foam of identical formulation but not containing a flameproofing agent, hereafter referred to as foam R, and secondly a foam identical to foam A but containing, as a flameproofing agent, the known diethyl diethanolaminomethylphosphonate, which will be referred to as foam B.

The amount of flameproofing agent incorporated into foams A and B was such that each foam had a phosphorus content of 1% by weight.

The foams A, B and R all had a density of 50 g/liter. These foam samples were subjected to the "limiting oxygen index" (LOI) test according to Standard Specification ASTM D 2863 (see C. P. Fenimore and F. J. Martin "Modern Plastics", 44, 141, 1966). The higher the LOI index, the greater the flameproofing power of the additive added to the polyurethane foam.

The foam samples were also subjected to the following tests:
measurement of the delay in self-ignition under a given heat flux, and
measurement of the rate of combustion in air, in a vertical and horizontal configuration.

Table I below gives the results obtained.

TABLE I

| foam | LOI index | delay in self-ignition (seconds) | rate of combustion (mm/sec) | |
|---|---|---|---|---|
| | | | vertical | horizontal |
| A | 0.201 | 5.6 | 2.30 | 4.7 |
| B | 0.198 | 4.7 | 2.11 | 5.5 |
| R | 0.172 | 5.2 | 4.6 | 8.0 |

From the results shown in Table I, it may be seen that foam A flameproofed with the carbamate according to the invention had, for the same phosphorus content, improved resistance compared to foam B both as regards the delay in self-ignition and as regards the rate of combustion in a horizontal configuration.

The mechanical properties of the foams A, B and R were also determined by measuring the compressive strength of the foam samples. The critical pressure of the foam, that is to say the limiting pressure beyond which the deformation of the foam is no longer elastic, was measured.

The results obtained are given in Table II below.

TABLE II

| foam | critical pressure Pc (bars) | variation in Pc in % relative to the critical pressure of the foam R |
|---|---|---|
| R | 3.9 | |
| A | 2.8 | − 25 |
| B | 2.3 | − 38 |

From Table II it may be seen that for foams of the same density, the decrease in critical pressure relative to that of foam R for foam A (flameproofed by means of the compound according to the invention) was less than that for foam B which contained a reactive flameproofing additive known for its ability to preserve the good mechanical properties of the foams in which it is incorporated.

To determine their aging resistance, foams A, B and R were subjected to the following two tests:
aging in a dry atmosphere for 22 hours at 140° C, and
moist aging by immersion in water for 144 hours at ambient temperature.

In both cases, the variations in critical pressure Pc of a given foam as a function of aging were compared, using the formula:

$$\frac{Pcv - Pci}{Pci} \times 100$$

wherein
$Pcv$ = critical pressure after aging
and
$Pci$ = critical pressure before aging.

Table III gives the results obtained after these aging tests.

TABLE III

| foam | loss in mechanical properties in % | |
|---|---|---|
| | moist aging | aging in a dry atmosphere |
| A | + 17 | + 10 |
| B | − 11 | − 8 |
| R | + 5 | − 6 |

It was found that, contrary to foam B, foam A, after aging, had mechanical properties similar to, or rather better than, those of the reference foam R.

Finally, the fumes emitted during flameless combustion and combustion with flames, of standardised samples of foams A, B and R, in a fume chamber of the N.B.S. (National Bureau of Standards) type, were compared qualitatively and quantitatively. Using this apparatus, it was possible to determine, as a function of time, the specific optical density or the attenuation of a light beam which passed through the fumes, represented by the optical density measured over a unit optical path in a chamber of unit volume, starting from a sample of unit surface area. In other words, if the specific optical density of the sample in question is called Ds, the following equation applies:

$$Ds = Dexp \frac{V}{AL} = \frac{V}{AL} \log \frac{F_o}{F}$$

where
- $F_o$ = intensity of the incident light
- $F$ = intensity of the transmitted light
- $V$ = volume of the chamber
- $A$ = surface area of the emitting sample
- $L$ = optical path.

The concentrations of hydrocyanic acid, carbon monoxide, and nitrogen oxides in the gases evolved during the combustion of the samples were also determined.

Table IV gives the results obtained.

TABLE IV

| foam | specific optical density | | combustion gas in ppm (tests with flame) | | |
|---|---|---|---|---|---|
| | without flame | with flame | CO | HCN | NO+NO$_2$ |
| A | 237 | 673 | 350 | 21 | 10 |
| B | 328 | 689 | 900 | 20 | 130 |
| R | 233 | 175 | 1000 | 20 | 120 |

It may be seen that foam A flameproofed by a compound of the invention emitted less fumes and less toxic gases than foam B flameproofed by the known compound.

Further examples of formulations of rigid polyurethane foams, hereafter designated foams C, D and E, are given below. The carbamates according to the invention used in these formulations were reaction products of diethyl hydroxymethylphosphonate chloroformate with, respectively, piperidine (compound 3, foam C), diethylamine (compound 2, foam D) and aniline (compound 5, foam E), obtained as described above.

| | C | D | E |
|---|---|---|---|
| Polyol TP 440 (trimethylolpropane epoxidised with propylene oxide) | 100 g | 100 g | 100 g |
| Methylene-diphenylisocyanate | 104 g | 104 g | 104 g |
| Rhodorsil SI 190 (silicone) | 1 g | 1 g | 1 g |
| Dibutyl-tin dilaurate | 0.15 g | 0.15 g | 0.15 g |
| Freon (trichlorofluoroethane) | 30 g | 30 g | 30 g |
| Carbamate-phosphonate obtained from piperidine | 1 g | | |
| Carbamate-phosphonate obtained from diethylamine | | 1 g | |
| Carbamate-phosphonate obtained from aniline | | | 1 g |
| Density | 47 g/l | 44 g/l | 40 g/l |
| Phosphorus content (%) | 1 % | 1 % | 0.85 % |

Samples of foams C, D and E were subjected to tests to determine the limiting oxygen index (LOI) in accordance with the standard test for rigid foams, and to determine the rate of combustion in air in a vertical and horizontal configuration.

The results of these tests, compared to those obtained with foam B described above (flameproofed by means of diethyl diethanolaminomethylphosphonate), are shown in Table V below:

TABLE V

| foam | LOI index | rate of combustion mm/sec. | |
|---|---|---|---|
| | | vertical | horizontal |
| B | 0.198 | 2.11 | 5.5 |
| C | 0.194 | 1.52 | 4.56 |
| D | 0.193 | 1.75 | 5.08 |
| E | 0.194 | 1.93 | 5.80 |

From Table V it may be seen that, for the same phosphorus content, foams C, D and E containing flameproofing agents according to the invention, exhibited a rate of combustion approximately equal to or slightly less than that of foam B containing the known additive.

The results of the above-mentioned tests show that the carbamates according to the invention, when compared with the known flameproofing additive, imparted better mechanical stability and good aging resistance, in both dry and wet atmospheres, to rigid polyurethane foam. Compared with the known additive, the carbamates according to the invention exhibited at least a comparable performance when exposed to fire, and provided a significant improvement in respect of the amount of fumes evolved during flameless combustion and combustion with flames.

Whilst, up to now, it has generally been found that reactive additives are suitable only for rigid foams and that non-reactive additives could be used equally well in rigid foam and in flexible foam formulations, we have found, unexpectedly, that the carbamates according to the invention, whether reactive or non-reactive, are equally suitable for use in both flexible foams and rigid foams.

An example of a formulation (in parts by weight) of a flexible foam (foam F) containing the preferred compound of the invention (1) is given below:

| | |
|---|---|
| Napiol C50 (Trade Mark registered by Naphta Chimie for hydroxylic polyethers) | 100 |
| Toluenediisocyanate | 32 |
| Water | 2 |
| N-Methylmorpholine | 0.8 |
| Dibutyl-tin dilaurate | 0.15 |
| Silicone agent SI 190 | 1 |
| N,N-Bis-(2-hydroxyethyl)-carbamate of diethyl methylphosphonate | 12 |

A flexible foam prepared from the formulation had a density of 89 g/l and a phosphorus content of 1.01% by weight.

Although the flameproofing agent employed was a reactive additive, no difficulty was experienced in preparing the flexible foam.

What is claimed is:

1. Carbamate-phosphonates of the formula:

$$\begin{array}{c} C_2H_5O \\ \phantom{C_2H_5O} \diagdown \\ \phantom{C_2H_5O \diagdown} P-CH_2-O-CO-N \diagup^{R_1}_{\diagdown R_2} \\ \phantom{C_2H_5O} \diagup \| \\ C_2H_5O \phantom{\diagup} O \end{array}$$

wherein $R_1$ and $R_2$ are the same or different and are linear or branched alkyl or hydroxyalkyl radicals containing 2 or 3 carbon atoms or $R_1$ and $R_2$ together with the nitrogen atom to which they are attached form a 5 or 6 member ring containing one nitrogen atom and 4 or 5 carbon atoms, or $R_1$ is phenyl and $R_2$ is hydrogen.

2. The N,N-bis-(2-hydroxyethyl)-carbamate of diethyl methylphosphonate.

3. The N,N-diethylcarbamate of diethyl methylphosphonate.

4. The N-cyclotetramethylene-carbamate of diethyl methylphosphonate.

5. The N-cyclopentamethylene-carbamate of diethyl methylphosphonate.

6. The phenylcarbamate of diethyl methylphosphonate.

7. A method of preparing a carbamatephosphonate of formula

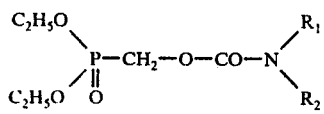

wherein $R_1$ and $R_2$ are the same or different and are linear or branched alkyl or hydroxyalkyl radicals containing 2 or 3 carbon atoms or $R_1$ and $R_2$ together with the nitrogen atom to which they are attached form a 5 or 6 member ring containing one nitrogen atom and 4 or 5 carbon atoms, or $R_1$ is phenyl and $R_2$ is hydrogen which comprises dissolving an amine which is a member selected from the group consisting of secondary alkylamines, the alkyl groups of which each contain 2 or 3 carbon atoms, dialkanolamines the hydroxyalkyl groups of which each contain 2 or 3 carbon atoms, aniline, pyrrolidine and piperidine, in an aqueous phase containing an alkali base, introducing therein a solution of diethyl hydroxymethyl phosphonate chloroformate in an organic solvent which is immiscible with water and inert towards said diethyl hydroxymethyl phosphonate chloroformate, allowing the reaction to occur by interfacial condensation at a temperature below 10° C and isolating said carbamate-phosphonate from the reaction mixture.

8. A method according to claim 7, in which the organic solvent is immiscible with water, inert towards the chloroformate, and a solvent for the reaction product.

9. A method for the preparation of the N,N-diethylcarbamate of diethyl methylphosphonate according to claim 7, which comprises reacting equimolecular amounts of diethyl hydroxymethylphosphonate chloroformate and diethylamine in solution in anhydrous ether, and in the presence of triethylamine.

10. A method according to claim 8, for the preparation of the N,N-bis-(2-hydroxyethyl)-carbamate of diethyl methylphosphonate which comprises bringing an aqueous phase, containing diethanolamine in an excess of more than about 5% and up to about 30% of the stoichiometric amount and an alkali metal carbonate, into contact with an organic phase comprising diethyl hydroxymethylphosphonate chloroformate dissolved in chloroform, whilst stirring at a temperature between about 0° C and 5° C, separating off the organic phase and washing it, and removing solvent from the organic phase by evaporation under reduced pressure.

* * * * *